US012398485B2

(12) United States Patent
Wei et al.

(10) Patent No.: US 12,398,485 B2
(45) Date of Patent: Aug. 26, 2025

(54) METHOD OF DETECTING CRYSTALLOGRAPHIC DEFECTS AND METHOD OF GROWING AN INGOT

(71) Applicants: Zing Semiconductor Corporation, Shanghai (CN); Shanghai Institute of Microsystem and Information Technology, Chinese Academy of Sciences, Shanghai (CN)

(72) Inventors: Xing Wei, Shanghai (CN); Yun Liu, Shanghai (CN); Xun Wang, Shanghai (CN); Zhongying Xue, Shanghai (CN)

(73) Assignees: Zing Semiconductor Corporation, Shanghai (CN); SHANGHAI INSTITUTE OF MICROSYSTEM AND INFORMATION TECHNOLOGY, CHINESE ACADEMY OF SCIENCES, Shanghai (CN)

( * ) Notice: Subject to any disclaimer, the term of this patent is extended or adjusted under 35 U.S.C. 154(b) by 656 days.

(21) Appl. No.: 17/721,949

(22) Filed: Apr. 15, 2022

(65) Prior Publication Data
US 2022/0333269 A1    Oct. 20, 2022

(30) Foreign Application Priority Data
Apr. 16, 2021    (CN) .......................... 202110412646.0

(51) Int. Cl.
*G01N 21/95* (2006.01)
*C30B 15/20* (2006.01)
(Continued)

(52) U.S. Cl.
CPC ............ *C30B 15/203* (2013.01); *C30B 29/06* (2013.01); *G01N 21/9505* (2013.01); *G01N 33/0095* (2024.05)

(58) Field of Classification Search
CPC ..... C30B 15/203; C30B 29/06; C30B 23/002; C30B 15/20; G01N 21/9505;
(Continued)

(56) References Cited

U.S. PATENT DOCUMENTS

| 6,879,925 B1 * | 4/2005 | Sasagawa .......... G01R 31/2858 |
|---|---|---|
| | | 702/123 |
| 2006/0289386 A1 * | 12/2006 | Tysoe ................ H01L 21/31111 |
| | | 73/705 |

(Continued)

OTHER PUBLICATIONS

Chinese Office Action, dated Oct. 24, 2023, and Search Report dated Oct. 20, 2023, in a counterpart Chinese patent application, No. CN 202110412646.0.
(Continued)

*Primary Examiner* — Alvaro E Fortich
(74) *Attorney, Agent, or Firm* — Chen Yoshimura LLP (57) ABSTRACT

The invention provides a method of detecting crystallographic defects, comprising: sampling wafer of an ingot in complying with a predetermined wafer sampling frequency; identifying crystallographic defects of the wafer to show the crystallographic defects of the wafer; characterizing observation of the crystallographic defects of the wafer and extracting a value characterizing the crystallographic defects; through a result of characterizing the crystallographic defects, obtaining a radial distribution of density of the wafer and categorizing the crystallographic defects; and obtaining an isogram of the crystallographic defects of the wafer to show a crystallographic defect distribution of the whole ingot according to the value characterizing the crystallographic defects and categories of the crystallographic defects. It is no need to break the ingot to obtain the crystallographic defect distribution of the whole ingot,
(Continued)

through which the technology for growing the ingot may be effectively adjusted to obtain the ingot with required characteristics of defect.

9 Claims, 5 Drawing Sheets

(51) Int. Cl.
  *C30B 29/06* (2006.01)
  *G01N 33/00* (2006.01)
(58) Field of Classification Search
  CPC ........... G01N 33/0095; G01N 21/9501; G01N 21/8851; G01N 2021/8874
  See application file for complete search history.

(56) References Cited

U.S. PATENT DOCUMENTS

| | | | |
|---|---|---|---|
| 2008/0311342 A1* | 12/2008 | Muller | C30B 15/203 428/134 |
| 2009/0217866 A1 | 9/2009 | Goto et al. | |
| 2013/0186144 A1* | 7/2013 | Miyamoto | C30B 15/08 65/90 |
| 2014/0220713 A1* | 8/2014 | Dowski, Jr. | H01L 27/14627 438/15 |
| 2017/0160335 A1* | 6/2017 | Aratani | C30B 29/06 |
| 2017/0260651 A1* | 9/2017 | Robinson | H01L 21/02444 |

OTHER PUBLICATIONS

Liu et al., "Characterization of grown-in defects in Si wafers by gas decoration", Materials Science in Semiconductor Processing, 2021, vol. 130, No. 105822, p. 1-7.

Sun et al., "Axial distribution of bulk micro-defects in Czochralski single crystal silicon", Proceedings of Tianjin Electronic Industries Association 2020 Annual Conference, Jun. 2020, p. 2-5 English abstract is attached.

Chinese Office Action, dated Apr. 20, 2024, and Search Report dated Apr. 19, 2024, in a counterpart Chinese patent application, No. CN 202110412646.0.

* cited by examiner

METHOD OF DETECTING CRYSTALLOGRAPHIC DEFECTS AND METHOD OF GROWING AN INGOT

FIELD OF THE INVENTION

The present invention generally relates to semiconductor technical field, and specifically, relates to a method of detecting crystallographic defects and a method of growing an ingot.

BACKGROUND OF THE INVENTION

Defects introduced during monocrystalline silicon growth may affect yield of semiconductor devices to a great extent. Different devices are sensitive to different types of defects and density of defect. Therefore, it is needed to detect the growth of monocrystalline silicon.

Generally, current methods of detecting crystallographic defects are performed with wafer sampling test. The wafer may be tested through laser scattering tomography (LST), copper modification, bulk micro defect (BMD) technology, etc. However, these technologies always fail to characterize the whole defects or require for long period of experiment, and meanwhile face errors due to a small quantity of sampling. Accurate distribution of defect is only obtained through observing a longitudinal faction of an ingot that makes the ingot broken to increase cost as production loss.

Thus, it is needed a simple, efficient and economic method to detect defects in a monocrystalline silicon product and guide adjustment, debugging and modification of monocrystalline silicon growth, so as to generate a monocrystalline silicon with required characteristics of defect.

SUMMARY OF THE INVENTION

Aiming on the problem of the current technology, the present invention provides a method of detecting crystallographic defects and a method of growing an ingot to solve problems of failing to characterize crystallographic defects of a whole ingot, overlong experiment period and excessive cost.

In an embodiment of the invention, optionally, the present invention may provide a method of detecting crystallographic defects, comprising: sampling wafer of an ingot in complying with a predetermined wafer sampling frequency; identifying crystallographic defects of the wafer to show the crystallographic defects of the wafer; characterizing observation of the crystallographic defects of the wafer and extracting a value characterizing the crystallographic defects; through a result of characterizing the crystallographic defects, obtaining a radial distribution of density of the wafer and categorizing the crystallographic defects; and obtaining an isogram of the crystallographic defects of the wafer to show a crystallographic defect distribution of the whole ingot according to the value characterizing the crystallographic defects and categories of the crystallographic defects.

In an embodiment of the invention, optionally, the categories of the crystallographic defects may comprise vacancy defect and self-interstitial defect.

In an embodiment of the invention, optionally, the step of identifying crystallographic defects of the wafer may comprise technologies of vapor phase epitaxial (VPE) deposition, gas etching, copper modification and bulk micro-defect (BMD) heat treatment.

In an embodiment of the invention, optionally, the step of characterizing observation of the crystallographic defects of the wafer may comprise observing the crystallographic defects of the wafer with one of an optical microscope, light scattering tomography, laser light scattering and minority carrier lifetime.

In an embodiment of the invention, optionally, the step of sampling wafer of an ingot may be performed along with a longitudinal direction of the ingot.

In an embodiment of the invention, optionally, the predetermined wafer sampling frequency may be $1/10$ millimeter$^{-1}$ (mm$^{-1}$)~$1/200$ mm$^{-1}$.

In an embodiment of the invention, optionally, the step of obtaining an isogram of the crystallographic defects of the wafer may comprise inputting the value characterizing the crystallographic defects and categories of the crystallographic defects into an analog editor to draw the isogram of the crystallographic defects of the wafer, and the analog editor is one of MATLAB analog editor or Python analog editor.

In an embodiment of the invention, optionally, the present invention may provide a method of growing an ingot, comprising: sampling wafer of an ingot in complying with a predetermined wafer sampling frequency; identifying crystallographic defects of the wafer to show the crystallographic defects of the wafer; characterizing observation of the crystallographic defects of the wafer and extracting a value characterizing the crystallographic defects; through a result of characterizing the crystallographic defects, obtaining a radial distribution of density of the wafer and categorizing the crystallographic defects; obtaining an isogram of the crystallographic defects of the wafer to show a crystallographic defect distribution of the whole ingot according to the value characterizing the crystallographic defects and categories of the crystallographic defects; and adjusting a technology for growing the ingot according to the crystallographic defect distribution of the whole ingot to obtain the ingot with required characteristics of defect.

In an embodiment of the invention, optionally, the step of adjusting a technology for growing the ingot may comprise lowering a pulling rate of the ingot or raising a temperature gradient when the crystallographic defects are vacancy defects.

In an embodiment of the invention, optionally, the step of adjusting a technology for growing the ingot may comprise raising a pulling rate of the ingot or lowering a temperature gradient when the crystallographic defects are self-interstitial defects.

Compared with current technologies, in the method of detecting crystallographic defects and the method of growing an ingot of the present invention, wafers of the ingot are sampled in complying with the predetermined wafer sampling frequency, the crystallographic defects of the wafer are identified to observe the characteristics, the value characterizing the crystallographic defects is extracted, radial distribution of density of the wafer is obtained and the crystallographic defects are categorized through the result of characterizing the crystallographic defects, and the value characterizing the crystallographic defects and the categories of the crystallographic defects are input into the analog editor to draw the isogram of the crystallographic defects of the wafer and obtain the crystallographic defect distribution of the whole ingot. Through aforesaid methods, it is no need to break the ingot to obtain the crystallographic defect distribution of the whole ingot, through which the technology for growing the ingot may be effectively adjusted to obtain the ingot with required characteristics of defect.

BRIEF DESCRIPTION OF THE DRAWINGS

Various objects and advantages of the present invention will be more readily understood from the following detailed description when read in conjunction with the appended drawing, in which.

DESCRIPTION OF EMBODIMENTS OF THE INVENTION

Reference is now made to the following examples taken in conjunction with the accompanying drawings to illustrate detailed implementation of the present invention. Persons of ordinary skill in the art having the benefit of the present disclosure will implement the present invention without at least one of the details disclosed here. Please note that common knowledge in the art may not be illustrated here to avoid from obscurity.

The present disclosure illustrates various aspects of the embodiments according to the present invention, which may be implemented in various ways. Please note that embodiments described here are only for example and those skilled in the art should understand that any one of the aspects may not be limited to them. With the disclosure of the embodiments, those skilled in the art may readily understand the scope of the present invention. Please also note that the figures provided here are only exemplary. Only elements relative to the invention are shown therein. Actual number, shape, sizes, type and proportion may be varied in an implementation. For clarity, sizes or relative sizes of layers, regions, etc. may be exaggerated. The same reference number designates the same element. Layout or arrangement may be more complicated.

Figure 1:
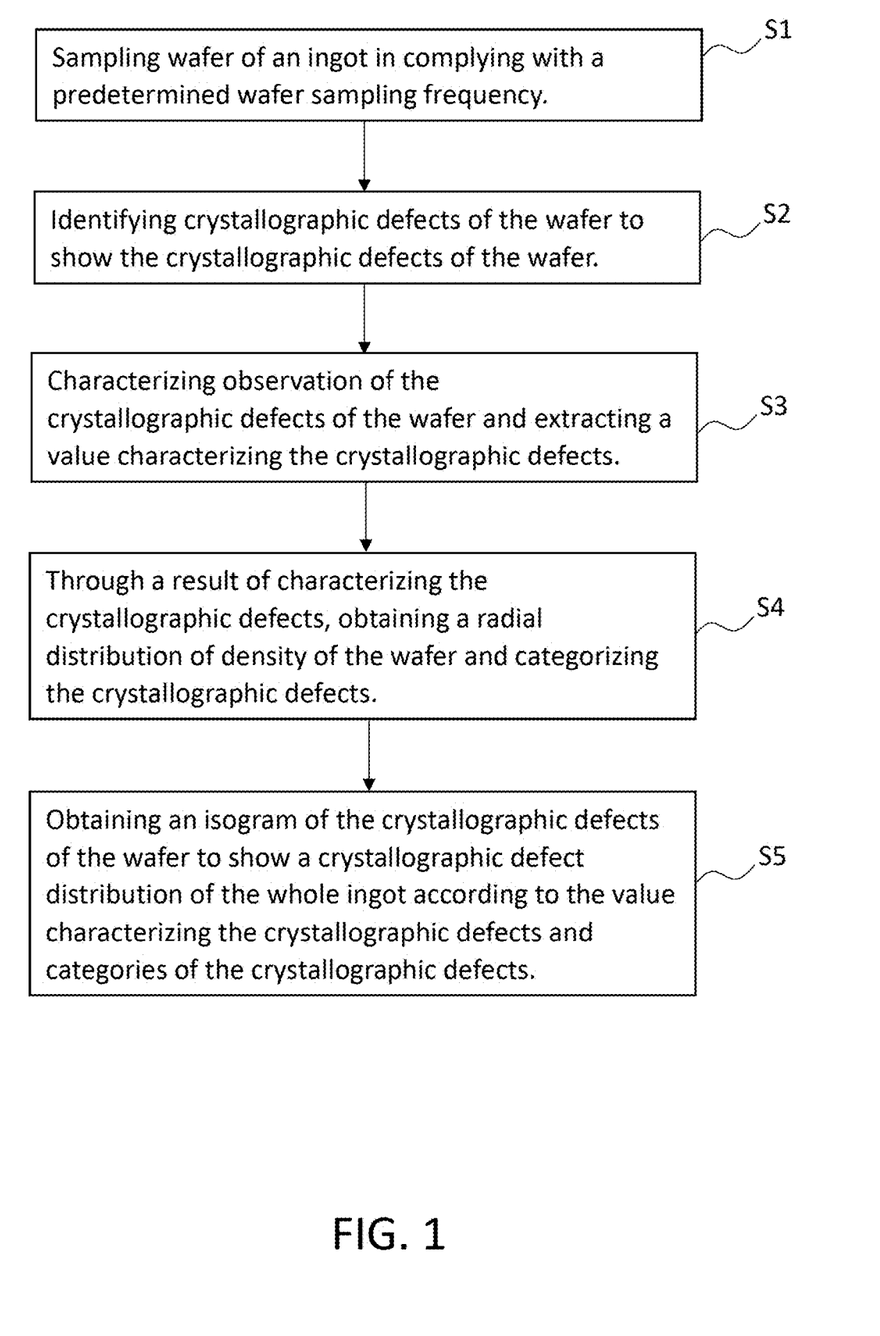
FIG. 1 shows a flow chart of a method of detecting crystallographic defects in an embodiment according to the invention.

FIG. 1 shows a flow chart of a method of detecting crystallographic defects in an embodiment according to the invention. As shown in FIG. 1, the present invention may provide a method of detecting crystallographic defects, comprising: step S1: sampling wafer of an ingot in complying with a predetermined wafer sampling frequency; step S2: identifying crystallographic defects of the wafer to show the crystallographic defects of the wafer; step S3: characterizing observation of the crystallographic defects of the wafer and extracting a value characterizing the crystallographic defects; step S4: through a result of characterizing the crystallographic defects, obtaining a radial distribution of density of the wafer and categorizing the crystallographic defects; and step S5: obtaining an isogram of the crystallographic defects of the wafer to show a crystallographic defect distribution of the whole ingot according to the value characterizing the crystallographic defects and categories of the crystallographic defects.

FIGS. 2~5 show schematic views of structure corresponding to the method of detecting crystallographic defects in an embodiment according to the invention. Here, the method of detecting crystallographic defects is introduced with reference to FIGS. 2~5.

Figure 2:
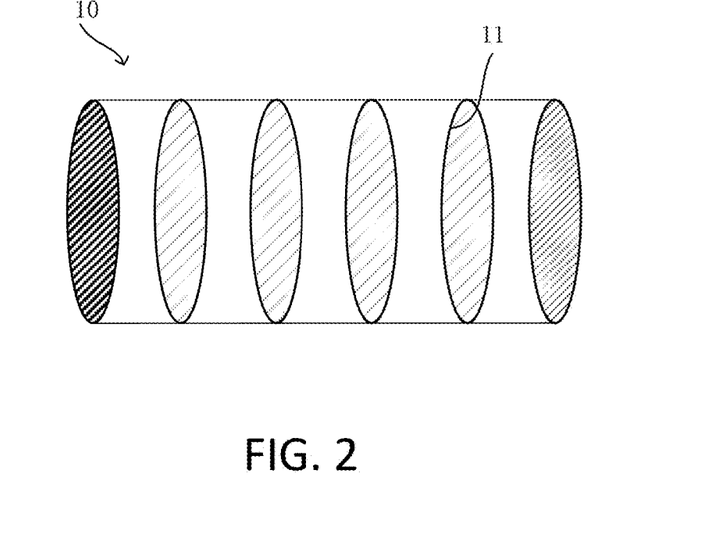
FIGS. 2~5 show schematic views of structure corresponding to the method of detecting crystallographic defects in an embodiment according to the invention.

Referring to FIG. 2, in a step S1, wafers of an ingot 10 are sampled in complying with a predetermined wafer sampling frequency. In the present embodiment, the sampling is performed along with a longitudinal direction of the ingot 10. The predetermined wafer sampling frequency may be $\frac{1}{10}$ mm$^{-1}$~$\frac{1}{200}$ mm$^{-1}$. Sampling in complying with the predetermined wafer sampling frequency may facilitate reflect the growth of the crystallographic defects in the whole ingot.

Figure 3:
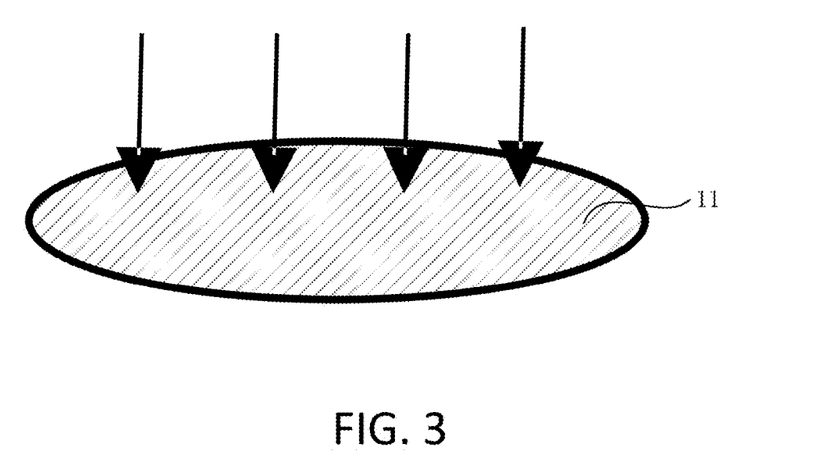

Referring to FIG. 3, in an step S2, the crystallographic defects of the wafer 11 may be identified to show the crystallographic defects of the wafer 11. The way to identify the crystallographic defects may comprise technologies of vapor phase epitaxial (VPE) deposition, gas etching, copper modification and bulk micro-defect (BMD) heat treatment. Specifically, VPE deposition may deposit silicon on the wafer 11. When the crystallographic defects exist on the wafer 11, deposition rate of silicon in an region in which the crystallographic defects exist may be different from that of other area. After the deposition is finished, a thickness of silicon on the wafer 11 may be different, and therefore protrusion and recess which show the crystallographic defects are formed. A gas for performing VPE deposition may be $SiHCl_3$ for example. The thickness of silicon deposited on the wafer 11 may be within 0.5 μm~5 μm. Because different crystallographic defects exist on the wafer 11, different densities of crystallographic defect show, and different reaction rates present. A gas etching technology may be applied to corrode holes in various sizes, i.e. some are big, some are small, some are deep and some are shallow. A bulk micro-defect (BMD) heat treatment may be implemented as two-step heat treatment. Due to more surface defects on a bare silicon, minority carrier lifetime is too low to be measured. Therefore, it is needed to apply the BMD heat treatment. A copper modification technology may change appearance of the crystallographic defects of the wafer 11. Difference of appearance may be used to determine categories of the crystallographic defects and calculate a density of crystallographic defect.

In the present embodiment, the step of identifying crystallographic defects of the wafer may be performed with gas etching technology which may use 20 slm~80 slm hydrogen gas with introducing 0.1%~10% hydride of a group 7 element which may be HF, HCl, HBr, HI for example. In the present embodiment, HCL is served as the hydride of a group 7 element, reaction temperature for performing the gas etching step is within 700□~1100□ for example, and preferably, at 900□.

Figure 4:
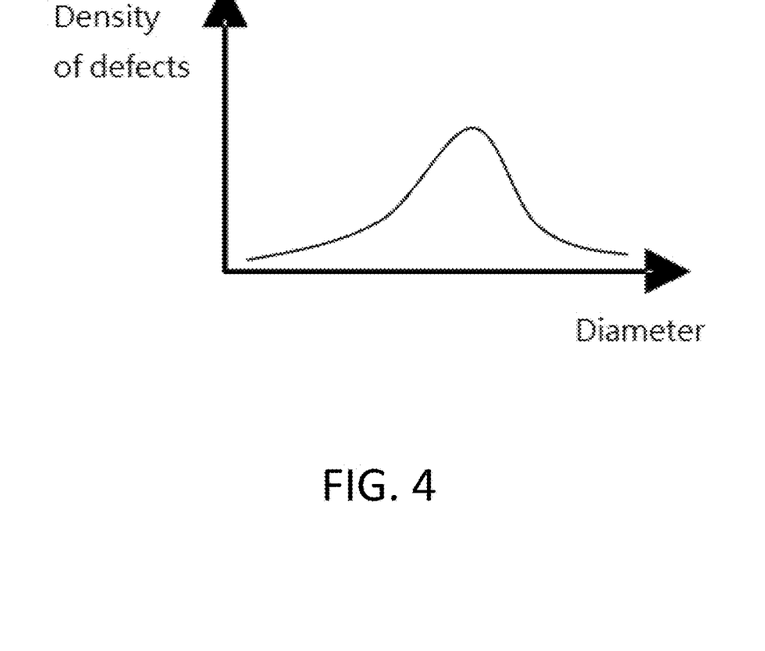

Referring to FIG. 4, in a step S3, characteristics of the crystallographic defects of the wafer 11 are observed, and a value characterizing the crystallographic defects is extracted. In the present embodiment, the way to observe the crystallographic defects of the wafer may comprise observing with an optical microscope (OM), light scattering tomography (LST), laser light scattering (LLS) and minority carrier lifetime (MCLT).

When the crystallographic defects of the wafer 11 are identified with VPE deposition or gas etching technology, preferably, the way to observe the crystallographic defects may be LLS. LLS may calculate position and equivalent sizes of the protrusion or recess on the wafer 11 through scanning a surface of the wafer 11, and determine categories of the crystallographic defects through geometric distribution of the position of the crystallographic defects and the density of the crystallographic defects. When the crystallographic defects of the wafer 11 are identified with BMD heat treatment, preferably, the way to observe the crystallographic defects may be MCLT or LST. When the crystallographic defects of the wafer 11 are identified with copper modification, preferably, the way to observe the crystallographic defects may be OM, LLS, LST or MCLT.

In a step S4, through a result of characterizing the crystallographic defects, a radial distribution of density of the wafer 11 may be obtained, and the crystallographic defects may be categorized. In the present embodiment, the categories of the crystallographic defects may comprise vacancy defect and self-interstitial defect. A V region, a region of vacancy defect generated at a high pulling rate of the ingot or a low temperature gradient, may comprise V-rich (vacancy defects exist in this region), P-band (cores of OISF (oxidation induced stacking fault) s, i.e. large oxygen precipitations, exist in this region as defect) and Pv (small oxygen precipitations exist in this region as defects). An I region, a region of self-interstitial defect generated at a low pulling rate of the ingot or a high temperature gradient, may comprise A-defect (dislocation) and B-defect (self-interstitial radical). Defect-free is a region without any micro-defects. For the self-interstitial defect in the I region, copper modification may be applied to show the defects in a better way, but copper modification cannot show the vacancy defects in the V region well. For the vacancy defects in the V region, BMD heat treatment may be applied to show the defects in a better way, but BMD heat treatment cannot show the self-interstitial defects in the I region well.

Figure 5:
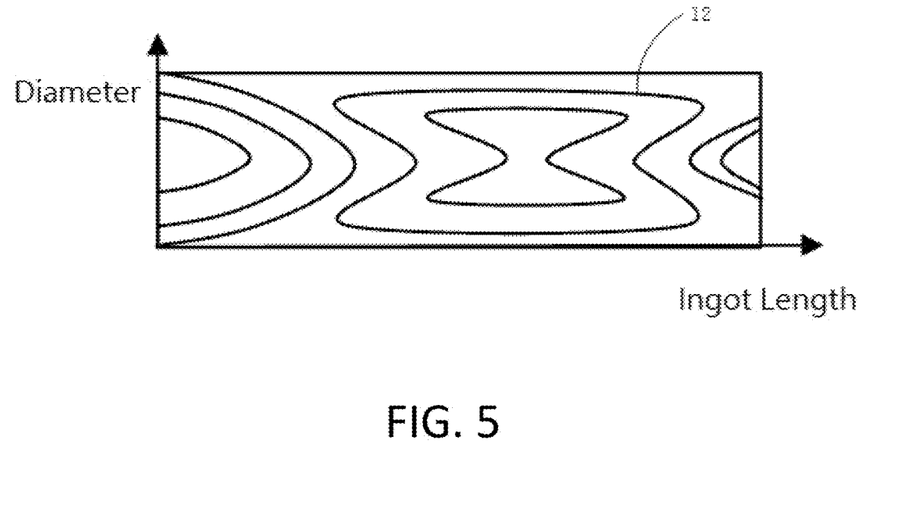

Referring to FIG. 5, in a step S5, the value characterizing the crystallographic defects and the categories of the crystallographic defects may be input into an analog editor to draw an isogram 12 of the crystallographic defects of the wafer 11, so as to show a crystallographic defect distribution of the whole ingot 10. In the present embodiment, the analog editor may be one of MATLAB analog editor or Python analog editor. As shown in FIG. 5, a horizontal axis represents length of the ingot 10, and vertical axis represents diameter of the ingot 10. FIG. 5 may show distribution of the crystallographic defect of the whole wafer 11.

Figure 6:
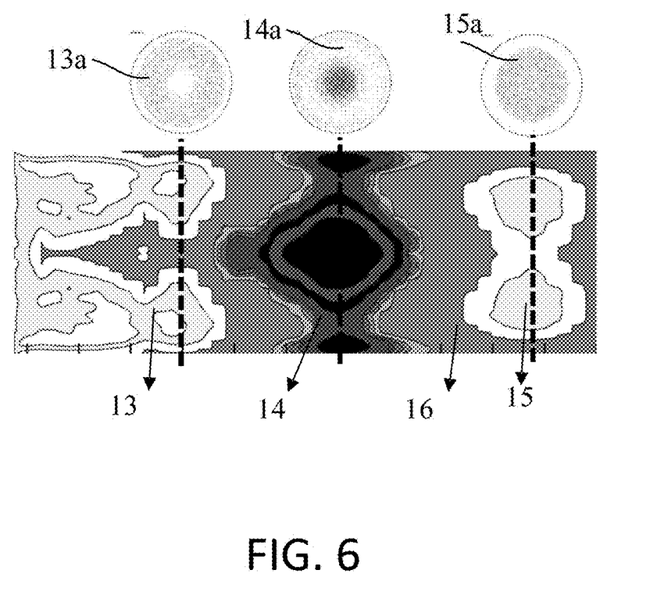
FIG. 6 shows a schematic view of distribution of crystallographic defects in an embodiment according to the invention.

FIG. 6 shows a schematic view of distribution of crystallographic defects in an embodiment according to the invention. As shown in FIG. 6, two ends of the ingot 10 belong to I regions 13, 15, a reference number 13a indicates a horizontal cross-sectional view of the I region 13 of the ingot 10, a reference number 15a indicates a horizontal cross-sectional view of the I region 15 of the ingot 10, the center of the ingot 10 belongs to V region 14, and a reference number 14a indicates a horizontal cross-sectional view of the V region 14 of the ingot 10.

Figure 7:
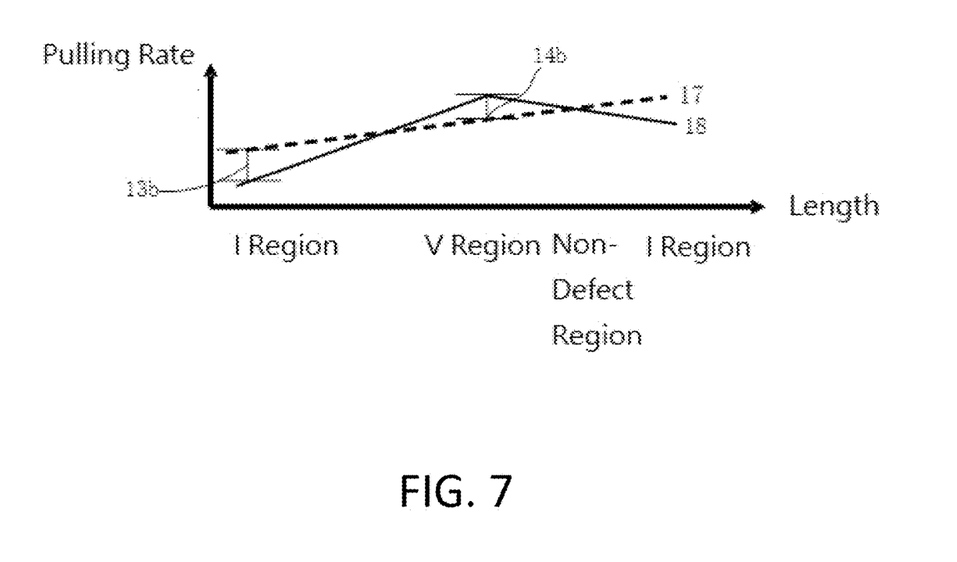
FIG. 7 shows a step of adjusting a technology for growing the ingot of a method of growing an ingot in an embodiment according to the invention.
Figure 8:
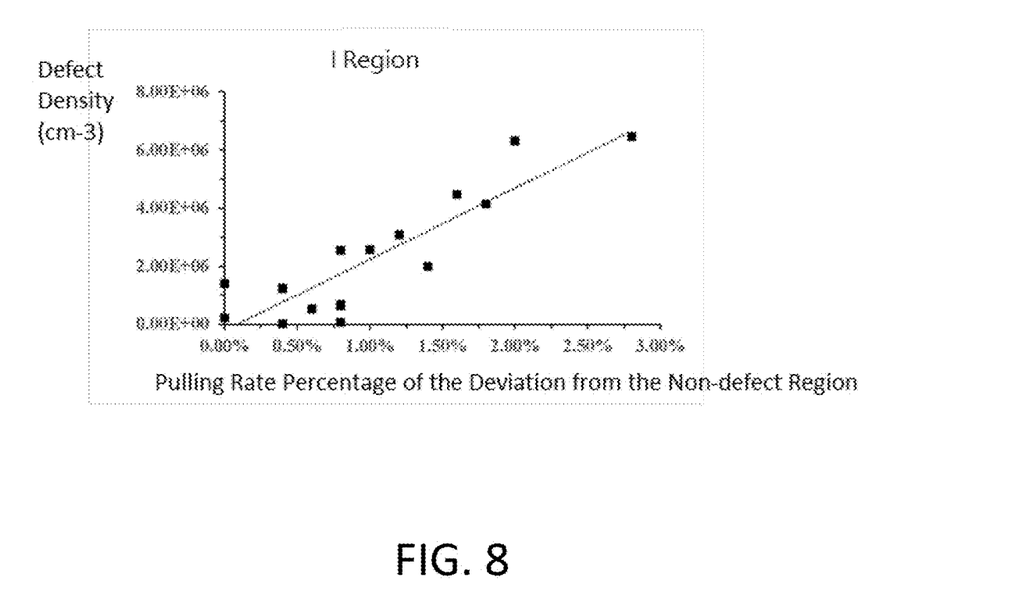
FIG. 8 shows a schematic view of adjusting the technology for growing the ingot in a I region of a method of growing an ingot in an embodiment according to the invention.
Figure 9:
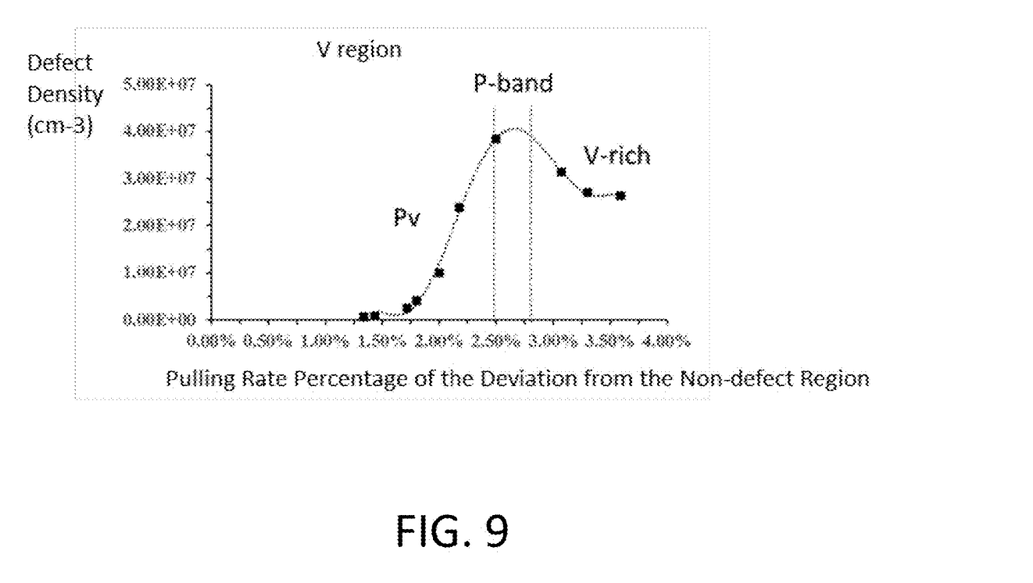
FIG. 9 shows a schematic view of adjusting the technology for growing the ingot in a V region of a method of growing an ingot in an embodiment according to the invention.

FIG. 7 shows a step of adjusting a technology for growing the ingot of a method of growing an ingot in an embodiment according to the invention, FIG. 8 shows a schematic view of adjusting the technology for growing the ingot in a I region of a method of growing an ingot in an embodiment according to the invention, and FIG. 9 shows a schematic view of adjusting the technology for growing the ingot in a V region of a method of growing an ingot in an embodiment according to the invention.

Referring to FIGS. 7~9, an embodiment of the present invention may provide a method of growing an ingot. The method is similar to the above method of detecting crystallographic defects, but additionally, comprises a step of adjusting a technology for growing the ingot 10 according to the crystallographic defect distribution of the whole ingot 10 to obtain the ingot 10 with required characteristics of defect.

In the present embodiment, the ingot 10 with required characteristics of defect means a perfect monocrystalline without intrinsic defects, such as a monocrystalline only has interstitial defects, a region without any defects gathering, or perfect monocrystalline such as monocrystalline only has interstitial defects and vacancy defects, or monocrystalline has a region of cores of small oxygen precipitations which is soluble at a high temperature.

In FIG. 7, corresponding pulling rate of each region is shown. A reference number 17 denotes a line of pulling rate for no defect, a reference number 18 denotes a line of actual pulling rate, a reference number 13b denotes a deviation of pulling rate of the line of actual pulling rate 18 of the I region and the line of pulling rate for no defect 17, and a reference number 14b denotes a deviation of pulling rate of the line of actual pulling rate 18 of the V region and the line of pulling rate for no defect 17. By comparing the deviation of pulling rate 13b of the line of actual pulling rate 18 of the I region and the line of pulling rate for no defect 17, shown in FIG. 7, with the correlation between pulling rate percentage of the deviation from the non-defect region of the I region, shown in FIG. 8, it may be readily understood that when the crystallographic defects are self-interstitial defects (i.e. in the I region), the pulling rate of the ingot may be raised or a temperature gradient may be lowered. By comparing the deviation of pulling rate 14b of the line of actual pulling rate 18 of the V region and the line of pulling rate for no defect 17, shown in FIG. 7, with the correlation between pulling rate percentage of the deviation from the non-defect region of the V region, shown in FIG. 9, it may be readily understood that when the crystallographic defects are vacancy defects (i.e. in the V region), the pulling rate of the ingot may be lowered or a temperature gradient may be raised.

As mentioned above, in the method of detecting crystallographic defects and the method of growing an ingot of the present invention, wafers of the ingot are sampled in complying with the predetermined wafer sampling frequency, the crystallographic defects of the wafer are identified to observe the characteristics, the value characterizing the crystallographic defects is extracted, radial distribution of density of the wafer is obtained and the crystallographic defects are categorized through the result of characterizing the crystallographic defects, and the value characterizing the crystallographic defects and the categories of the crystallographic defects are input into the analog editor to draw the isogram of the crystallographic defects of the wafer and obtain the crystallographic defect distribution of the whole ingot. Through aforesaid methods, it is no need to break the ingot to obtain the crystallographic defect distribution of the whole ingot, through which the technology for growing the ingot may be effectively adjusted to obtain the ingot with required characteristics of defect.

It is readily understood that aforesaid embodiments are only for example but not intended to limit the scope of the present invention. Those skilled in the art may change or modify it without departing from the scope of the annexed claims. All the changes or modifications is comprised by the scope of the annexed claims.

What is claimed is:

1. A method of detecting crystallographic defects, comprising:
   sampling wafer of an ingot in complying with a predetermined wafer sampling frequency;
   identifying crystallographic defects of the wafer to show the crystallographic defects of the wafer;
   characterizing observation of the crystallographic defects of the wafer and extracting a value characterizing the crystallographic defects;
   through a result of characterizing the crystallographic defects, obtaining a radial distribution of density of the wafer and categorizing the crystallographic defects; and
   obtaining an isogram of the crystallographic defects of the wafer to show a crystallographic defect distribution of the whole ingot according to the value characterizing the crystallographic defects and categories of the crystallographic defects,
   wherein the step of identifying crystallographic defects of the wafer comprises vapor phase epitaxial (VPE) deposition, gas etching, copper modification and bulk micro-defect (BMD) heat treatment.

2. The method of detecting crystallographic defects according to claim 1, wherein the categories of the crystallographic defects comprise vacancy defect and self-interstitial defect.

3. The method of detecting crystallographic defects according to claim 1, wherein the step of characterizing observation of the crystallographic defects of the wafer comprises observing the crystallographic defects of the wafer with one of an optical microscope, light scattering tomography, laser light scattering and minority carrier lifetime.

4. The method of detecting crystallographic defects according to claim 1, wherein the step of sampling wafer of the ingot is performed along with a longitudinal direction of the ingot.

5. The method of detecting crystallographic defects according to claim 4, wherein the predetermined wafer sampling frequency is $1/10$ millimeter$^{-1}$ (mm$^{-1}$)~$1/200$ mm$^{-1}$.

6. The method of detecting crystallographic defects according to claim 1, wherein the step of obtaining the isogram of the crystallographic defects of the wafer comprises inputting the value characterizing the crystallographic defects and categories of the crystallographic defects into an analog editor to draw the isogram of the crystallographic defects of the wafer, and the analog editor is one of MATLAB analog editor or Python analog editor.

7. A method of growing an ingot, comprising:
   sampling wafer of an ingot in complying with a predetermined wafer sampling frequency;
   identifying crystallographic defects of the wafer to show the crystallographic defects of the wafer;
   characterizing observation of the crystallographic defects of the wafer and extracting a value characterizing the crystallographic defects;
   through a result of characterizing the crystallographic defects, obtaining a radial distribution of density of the wafer and categorizing the crystallographic defects;
   obtaining an isogram of the crystallographic defects of the wafer to show a crystallographic defect distribution of the whole ingot according to the value characterizing the crystallographic defects and categories of the crystallographic defects; and
   adjusting a technology for growing the ingot according to the crystallographic defect distribution of the whole ingot to obtain the ingot with required characteristics of defect,
   wherein the step of identifying crystallographic defects of the wafer comprises vapor phase epitaxial (VPE) deposition, gas etching, copper modification and bulk micro-defect (BMD) heat treatment.

8. The method of growing an ingot according to claim 7, wherein the step of adjusting the technology for growing the ingot comprises lowering a pulling rate of the ingot or raising a temperature gradient when the crystallographic defects are vacancy defects.

9. The method of growing an ingot according to claim 7, wherein the step of adjusting the technology for growing the ingot comprises raising a pulling rate of the ingot or lowering a temperature gradient when the crystallographic defects are self-interstitial defects.

* * * * *